United States Patent [19]

Los

[11] 4,332,796

[45] Jun. 1, 1982

[54] POTENTIATED SULFONAMIDE INJECTABLE PREPARATION

[75] Inventor: Mario A. Los, Buenos Aires, Argentina

[73] Assignee: Laboratorios Bago S.A., Buenos Aires, Argentina

[21] Appl. No.: 158,398

[22] Filed: Jun. 11, 1980

[30] Foreign Application Priority Data

Feb. 19, 1980 [AR] Argentina ............................. 279998

[51] Int. Cl.³ ..................... A61K 9/42; A61K 31/505; A61K 31/625
[52] U.S. Cl. .................................... 424/229; 424/36; 424/38; 424/251
[58] Field of Search .................... 424/229, 251, 36, 38

[56] References Cited

U.S. PATENT DOCUMENTS

| | | | |
|---|---|---|---|
| 2,867,565 | 1/1959 | Feinstone | 424/229 |
| 3,551,564 | 12/1970 | Kläui et al. | 424/229 |
| 3,574,833 | 4/1971 | Arnold et al. | 424/229 |
| 4,031,214 | 6/1977 | Easterbrook | 424/229 |

FOREIGN PATENT DOCUMENTS

| | | | |
|---|---|---|---|
| 2804931 | 8/1979 | Fed. Rep. of Germany | 424/229 |
| 791750 | 3/1958 | United Kingdom | 424/229 |
| 1176395 | 11/1970 | United Kingdom | 424/229 |

*Primary Examiner*—Allen J. Robinson
*Attorney, Agent, or Firm*—Kane, Dalsimer, Kane, Sullivan and Kurucz

[57] ABSTRACT

Potentiated sulfonamide compositions useful for intramuscular injection are disclosed which comprise mixtures of alkali metal sulfonamides with microcrystalline potentiators wherein the microcrystals have been coated with mixtures of phospholipids and non-ionic surfactants. The compositions are advantageous in that they can be used extemporaneously by addition of sterile water for injection, the resulting aqueous preparation is stable for long periods of time and upon use the compositions are characterized by syringeability and lack of irritation at the injection site.

6 Claims, No Drawings

POTENTIATED SULFONAMIDE INJECTABLE PREPARATION

BACKGROUND OF THE INVENTION

1. Field of the Invention

The present invention is concerned with pharmaceutical injectable preparations comprising a potentiated sulfonamide for administration to mammals by the intramuscular route.

2. Brief Description of the Prior Art

The treatment of bacterial infections with sulfonamides has been known for several decades. Although their action on each microorganism differs due to cross resistance, a variety of these chemotherapeutic agents show similar potency. Their antibacterial activity is notably increased when sulfonamides are administered in combination with a potentiator agent of the 2,4-diaminopirimidine group (Brit. Med. J. 410 (8) 1978; Postgrad. Med. J., 45 (Suppl.) 56, 1969). According to this reference various combinations between sulfonamides and potentiators have been developed. The combinations vary either in the chemical structure of agents or in the proportion of sulfonamide and potentiator used in the preparation.

Several potentiated sulfonamides are described in the prior art (German Pat. Nos.: 2.445.440; 2.538.678; 2.627.706; 2.631.780; 2.638.052; and 2.818.281; Belgium Pat. No.: 851.060; Swiss Pat. No.: 544.053; Argentine Pat. Nos.: 172.760; 188.083; and 204.521). The prior art sulfonamide compounds have the following basic chemical structure:

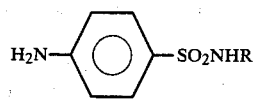
(I)

where R is substituted heterocycle, such as: pyridazine, pyrimidine, isoxazol and quinoxaline. For example, in the 4-amino-N-pyridazinylbenzene sulfonamide class there are: sulfamethoxy pyridazine and sulfaethoxy pyridazine. In the class of 4-amino-N (2- or 4-pyrimidinyl) benzene sulfonamides there are: sulfadoxine, sulfadiazine, sulfadimetoxine, sulfadimidine, sulfisomidine, sulfametoxidiazine and the like. Sulfametoxazol and sulfioxazol are representative 4-amino-N-(3'- or 5'-isoxazolyl) benzenesulfonamides. Another sulfonamide is sulfaquinoxaline (chemically named 4-amino-N (2-quinoxalinyl) benzenesulfonamide). Sulfamoxol is representative of a 4-amino-N (2-oxazolyl) benzenesulfonamide.

Potentiators used in combination with sulfonamides may be substituted 2,4-diaminopyrimidines of formula:

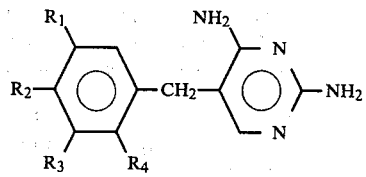
(II)

wherein $R_1$, $R_2$, $R_3$ and $R_4$ are each selected from hydrogen and methoxy groups. Representatives of the potentiators of Formula II are trimethoprim (5-3', 4', 5'-trimethoxy-benzyl)-2,4-diaminopyrimidine, ormethoprim (5-(3', 4'-dimethoxy -6'-methylbenzyl)-2,4-diaminopyrimidine) and diaveridine (5-3',4'-dimethoxybenzyl)-2,4-diaminopyrimidine).

The proportions of sulfonamide and potentiator used and described in the literature, is generally in a range of 1:1 to 20:1, preferably 5:1 (that is, 5 parts in weight of sulfonamide and 1 part in weight of potentiator).

Although the combination of sulfonamide and potentiator is more frequently used by oral route, several injectable preparations (which are able to give an antibacterial action faster than that obtained with tablets, capsules or suspensions) were previously known. During the development of the known injectable pharmaceutical preparations containing sulfonamides and their potentiator, several problems arose. According to the patent literature only a few of these problems were solved. For example, it is a very well known fact that sulfonamides are solubilized in water by the addition of pharmaceutically acceptable inorganic bases, such as sodium hydroxide, ammonium hydroxide or organic bases, such as triethanolamine, diethanolamine, monoethanolamine, meglumine and the like. However, potentiators such as those of the 2,4-diaminopyrimidine class (which have basic characteristics) are soluble in water only when they are salifyied with certain acids. The mixture of both solutions, gives a precipitate formed of the separate components. Precipitation of course impeded injectability of the preparation.

Another problem in the preparation of this kind of injectable formulation concerns its pH. When sulfonamides and potentiators are put into water at a pH near to 7, they may react giving an insoluble complex formed by one mole of sulfonamide and one mole of potentiator (see Japanese Patent No.: 73013511). To solve this problem, some investigators have followed two different courses. In the first course the components are first dissolved in water-miscible organic solvents, such as dimethylacetamide, ethanol, propyleneglycol, low molecular weight polyethyleneglycols and the like. In the second course, the sulfonamide is dissolved in water by the addition of bases, such as sodium hydroxide or diethanolamine and the potentiator, in microcrystalline form, is suspended in the solution. In the first case, that is, when water-miscible organic solvents are used, the resulting injectable preparations exhibit poor stability and provoke a high degree of irritation at the injection site. In some cases, irreversible tissue necrosis may occur. Several examples of these unstable, irritating preparations are known. For example, an injectable composition containing sodium sulfonamide and trimethoprim dissolved in a medium formed by polyethyleneglycol 400, ethanol, dimethylacetamide, diethanolamine and water is described in French Pat. No.: 1.523.606. Also, sulfonamide and trimethoprim have been dissolved in a mixture of water and dimethylacetamide (German Pat. No.: 2.445.400). In another injectable preparation (described in German Pat. No.: 2.538.678) sulfonamide and 2,4-diaminepyrimidine type potentiator are dissolved in a mixture of polyethyleneglycol, ethanol, citric acid, sodium hydroxyde and water. Other injectable solutions containing sulfonamide, trimethoprim, ethanol, propyleneglycol, polyvinylpyrrolidone and water are described in German Pat. Nos.: 2.631.779 and 2.631.780. Also representative of this state of the art is the disclosure found in U.S. Pat. No. 4,031,214.

Injectable suspensions of the prior art have the same stability problems associated with the solutions. They also pose other problems. For example, microcrystalline particles in suspension tend to form aggregates which precipitate in the bottom of vials and grow over a period of time. Consequently, the suspensions may not flow through needles commonly used for injections. The physical stability of these suspensions may be improved by adding certain vehicles which increase their viscosity. However, the increase of viscosity lowers syringeability. Another problem commonly observed in solutions as well as in suspensions, is the formation of small crystals of a sulfonamide-potentiator complex. The low diffusion of such a preparation at the injection site and the high pH (typically greater than 10), provoke local irritation and even irreversible necrosis (see Rasmussen, F.; Svensen, O.: Res. Vet. Sci., 20, 50 (1) 1976).

The present invention is of a potentiated sulfonamide preparation for injection, possessing greater stability than the prior art preparations, without the aforementioned problems. The preparations of the invention, upon intramuscular administration, do not provoke irritation or cause irreversible tissue alteration at the injection site. They exhibit excellent syringeability.

SUMMARY OF THE INVENTION

The invention comprises a pharmaceutical composition, which comprises; in admixture, (a) an alkali metal sulfonamide; and (b) microcrystals of a potentiator for such sulfonamide, said microcrystals being coated with a mixture of a phospholipid and a non-ionic surface-active agent. The compositions of the invention also include aqueous mixtures of the admixtures described above, which are useful for intramuscular administration to mammals, including humans, in need of sulfonamide therapy.

The invention also comprises the method of preparing the compositions of the invention and their use in treating mammals, including humans, for diseases responsive to sulfonamide treatment.

The term "microcrystal" as used herein means a crystal having a particle size (average diameter) within the range of from about $2\mu$ to about $40\mu$.

DETAILED DESCRIPTION OF THE INVENTION

Any of the previously known, pharmaceutically acceptable sulfonamides may be used in the method of the present invention and as ingredients of the compositions of the invention. The sulfonamides used in the compositions of the invention are preferably salified with an alkali metal, preferably sodium, prepared following known methods of synthesis. Generally they are obtained by dissolving sulfonamide in an alcoholic medium, adding an alkali hydroxide alcoholic solution, and precipitating the insoluble salt. The use of preformed sulfonamide alkaline salts instead of preparing them in situ in the final pharmaceutical product avoids an alkali excess in the final product. An alkali excess increases the potential for tissue injury at the injection site when the final product is used.

The potentiator component of the compositions of the invention preferably belonging to the 2,4-diaminepyrimidine class of compounds may be prepared by dissolving the potentiators in a water-alcohol medium and then precipitating it in microcrystalline form by the addition of an aqueous solution of a non-ionic surfactant and a phospholipid. In this way, potentiator microcrystals which have a size suitable to avoid syringeability problems are obtained, coated with surfactant and phospholipid. The coating on the microcrystals results in a stable suspension of the microcrystals in sterile water, without the aid of any suspending agent which might provoke not only a greater irritation at the injection site, but a lower chemotherapeutic diffusion in tissues and a decrease in injectability. This coating also prevents the microcrystal aggregation problems of the prior art. The good diffusion of this preparation in tissues is believed to be related to the coating of the microcrystals as described herein and improves syringeability of the compositions.

The non-ionic surface-active agents (surfactants) employed in the method of the invention is not critical as long as the one selected is pharmaceutically acceptable. Such surfactants are well known as is their preparation. Representative of such surfactants are the polyoxyalkylenesorbitan esters of fatty acids having 12–18 carbon atoms (with saturation or non-saturation of the hydrocarbon chain). Examples of such esters are the monooleates, monolaurates, monopalmitates and monostearates of polyoxyethylene sorbitan. Preferred are the monostearates and monopalmitates of polyoxyethylene sorbitan.

The particular phospholipid employed in the method of the invention is also not critical as long as it is pharmaceutically acceptable. Representative of such phospholipids are phosphatidylcholine, both naturally occurring and synthetically prepared, phosphatidic acid, lysophosphatidylcholine, phosphatidylserine, phosphatidylethanolamine, sphingolipids, phosphatidyglycerol, spingomyelin, cardiolipin, glycolipids, gangliosides, cerebrosides and the like used either singularly or intermixed such as in soybean phospholipids. Preferred are the phospholipids of the lecithin type, most preferably soy-bean lecithin.

The method of the invention for preparing the compositions of the invention may be carried out by coating microcrystals of the potentiator compound with the surfactant and phospholipid and then admixing the coated microcrystals with the sulfonamide.

Advantageously, the microcrystals of potentiator are formed simultaneously with the coating thereof. This is carried out by forming the microcrystals from an aqueous solution of potentiator compound in the presence of the non-ionic surfactant and the phospholipid as described above. As the microcrystals precipitate, they are coated with the surfactant and the phospholipid.

The ratio of proportions between surfactant and phospholipid may vary in a range of 1:30 to 1:70. A 1:50 ratio; that is, 1 part of phospholipid and 50 parts of surfactant is preferably used. The proportion ratio between potentiator:phospholipid:surfactant depends on the volume of the system and may vary between 100:1:30 and 300:1:70. Using a system of 1 part of ethanol to two parts of water, advantageous yields have been obtained. The proportions or ratio of sulfonamide to coated potentiator may be any of the proportions previously known and used for potentiated sulfonamide compositions.

The sterilization of solid compositions of the invention, i.e.; mixtures of sulfonamide alkali salt and coated potentiator may be carried out with ethylene oxide, which does not modify any physico-chemical property of the desired composition. The extemporaneous preparation of the injectable mixture with addition of sterile water for injection, brings a soluble sulfonamide alkali salt together with the surfactant-phospholipid coated potentiator micro crystals, in a system where the pH is in an advantageous range of 8.5–9.5. This is a pH lower than those found in previously known suspensions and is suitable to avoid the formation of undesired complexes. Furthermore, an extemporaneous pharmaceutical composition prepared by the method of the present invention has improved stability. The injection of this new potentiated sulfonamide injectable composition in mammals is perfectly tolerated and it provokes neither irritation nor local irreversible necrosis. The latter is probably due to the very small surfactant and phospholipid presence (less than 0.1%) which coat microcrystals in the compositions of the invention. The very small surfactant presence avoids foam formation which is generally found in injectable preparations containing higher amounts of surfactant. The high syringeability of the compositions of the invention, that is the ease with which the preparation flows through hypodermic needles, is another of its advantageous properties. This high syringeability is due in part to its low viscosity and because it is an aqueous suspension without the presence of any suspending agent or any other pharmaceutical aid. The coated microcrystals also resist aggregation.

One of the main advantages of this invention, is the low irritability of the injection site following injection of the compositions of the invention. Thus, while previously known injectable preparations provoke irritation at the injection site, even reaching irreversible necrosis, the pharmaceutical compositions herein described are less irritating.

Thus, using the process of the invention to obtain the new potentiated sulfonamide injectable compositions of the invention, that is the simultaneous coating and microcrystallization of potentiator, its mixture with the corresponding sodium sulfonamide and sterilization; gives new extemporaneous compositions. Their reconstitution, that is the addition of sterile water before use, provides a stable suspension characterized by a pH range of 8.5–9.5, good syringeability and low irritation at the injection site when administered to mammals.

The invention will be more fully explained in the following examples, which should not be considered as limiting the invention.

EXAMPLE I 39.4 g (0.156 moles) of sulfamethoxazol were suspended in 490 ml of isopropanol and then heated to 60° C. In a separate vessel a 1 N sodium hydroxide methanolic solution was prepared. 158 ml of the latter solution was heated and added to the suspension, with continuous stirring. After a few minutes the system became a solution, and then the salt began to precipitate. The reaction medium was cooled to 0°–5° C. and maintained at this temperature for two hours, the precipitate was filtered and washed with isopropanol (3×20 ml). The solid was dried at 40° C. for 10 hours under vacuum to obtain 33 g (Yield: 75.0%) of sodium sulfamethoxazol (p.m.p. 288°–290° C.; titrimetric assay 99.3%).

EXAMPLE II 9 g of sodium hydroxide were dissolved in 250 ml of methanol. Into another suitable container a suspension of sulfaquinoxaline in isopropanol was prepared (45 g; 0.15 moles, in 470 ml). The suspension was heated to a temperature of 40°–45° C., and the sodium hydroxide methanolic solution was added, with continuous stirring. After the complete dissolution of the suspended sulfaquinoxaline was achieved, a salt began to precipitate. The system was allowed to reach room temperature, maintaining continuous stirring, over a period of 3 hours. The precipitate was filtered, washed with isopropanol (3×30 ml) and dried, under vacuum at 40° C. to obtain 32.9 g (Yield: 68.1%) of sodium sulfaquinoxaline (m.p. over 300° C.; titrimetric assay 99.7%).

EXAMPLES III TO X

Following the general procedure described in Examples I and II, supra., but replacing the sulfonamides as used therein with other sulfonamides, the following sodium sulfonamides were prepared:

| COMPOUNDS | YIELD % | ASSAY % |
|---|---|---|
| Sodium Sulfamethoxypyridazine | 59.4 | 99.4 |
| Sodium Sulfaethoxypyridazine | 65.2 | 99.8 |
| Sodium Sulfadoxine | 74.3 | 99.4 |
| Sodium Sulfadiazine | 85.1 | 100.9 |
| Sodium Sulfametazone | 73.0 | 100.4 |
| Sodium Sulfisomidine | 75.2 | 99.8 |
| Sodium Sulfamethoxydiazine | 68.4 | 100.6 |
| Sodium Sulfamoxol | 76.6 | 100.2 |

EXAMPLE XI

Sorbitan monostearate polyoxyethylene (30 g) and soybean lecithin (0.6 g) were dissolved in demineralized water (2000 ml), with stirring at a temperature of 40° C. In a separate beaker a solution of trimethoprim, consisting of 60 g of trimethoprim in a solvent mixture of ethanol (600 ml) and water (300 ml), was prepared. The solution of trimethoprim was filtered and added to the first stirred solution, heated to 40° C. The resulting mixture was then cooled to a temperature of 0°–5° C., and after 2 hours the solid was filtered and then dried at 40° C. To obtain microcrystalline trimethoprim (50 g; Yield: 83.3%) coated with surfactant and lecithin.

EXAMPLE XII 1850 ml of an aqueous solution containing soybean lecithin (0.04%) and sorbitan monopalmitate polyoxyethylene (2%), was prepared. In another beaker, 60 g of diaverdine was dissolved in a solvent system of ethanol-isopropanol-ethyl acetate-water (50:10:5:35). The two solutions were heated to 40°–45° C., and then the diaverdine solution was slowly added into the first solution, with continuous stirring. The resulting microcrystalline suspension was cooled to a temperature of 15°–10° C., filtered and dried at 40° C., under vacuum to obtain 53 g (Yield: 88.3%) of microcrystalline diaveridine coated with surfactant and lecithin.

EXAMPLE XIII

Following the general procedure described in Example XI, supra., microcrystalline ormethoprim coated with surfactant and lecithin (Yield: 87.4%) was obtained.

EXAMPLE XIV

Sodium sulfamethoxazol (2.174 kg) obtained according to Example I, and microcrystalline trimethoprim (400 g) obtained according to Example XI, were poured into a stainless cylindrical tank mixer. The ingredients were mixed until an uniform powder was obtained and the powder was sterilized with ethylene oxide for 5 hours. The sterile mixture was fractionated into 10 ml vials (performing this operation in a clean room, class 100). Each vial contains 515 mg.

EXAMPLES XV TO XIX

Following the general procedure of Example XIV, supra., the following pharmaceutical preparations were prepared:

| EXAMPLE | ACTIVE INGREDIENTS SODIUM SULFONAMIDE | POTENTIATOR | AMOUNT PER VIAL (mg) | | ACID SULFONAMIDE: POTENTIATOR PROPORTION |
|---|---|---|---|---|---|
| XV | Sulfamoxol | Trimethoprim | 480① | (513)② | 5:1 |
| XVI | Sulfaquinoxaline | Diaveridine | 200 | (212) | 4:1 |
| XVII | Sulfadimethoxine | Trimethoprim | 480 | (508) | 5:1 |
| XVIII | Sulfadoxine | Ormethoprim | 400 | (425) | 7:1 |
| XIX | Sulfisoxazol | Ormethoprim | 450 | (483) | 7:2 |

① Weight expressed as acid sulfonamide + potentiator
② Actual weight

SYRINGEABILITY TEST

To the injectable preparations obtained in Examples XIV to XIX, 5 ml distilled water was added, and the pH and sedimentation times were measured. The results are shown in the following table. Using separate vials of the preparations obtained in Examples XIV to XIX, and using a 10 ml hypodermic syringe with a 20 gauge's needle, 5 ml of distilled water were poured into each vial. Each vial was gently shook for 30 seconds. Using the same syringe and needle, 5 ml of air was injected into each vial and the injectable suspension was allowed to fill the syringe. Each test was carried out with 10 vials, observing whether the suspension flows freely into the syringe or not. The test results are shown in the following table.

| ACTIVE INGREDIENTS* | pH | SEDIMENTATION TIME (minutes) | SYRINGEABILITY N° of assays/observed obstructions. |
|---|---|---|---|
| Sulfamoxol-Trimethoprim | 8.9–9.1 | 19 | 10/1 |
| Sulfaquinoxaline-diaveridine | 8.6–8.8 | 27 | 10/0 |
| Sulfadimethoxine-Trimethoprim | 8.7–9.0 | 20 | 10/0 |
| Sulfadoxine-Ormethoprim | 9.1–9.3 | 17 | 10/1 |
| Sulfisoxazol-Ormethoprim | 9.0–9.2 | 31 | 10/0 |
| Sulfamethoxazol-Trimethoprim | 9.0–9.2 | 25 | 10/0 |

*Sodium sulfonamides.

PHARMACOLOGICAL TESTS (Irritability Evaluation)

The pharmaceutical preparations obtained according to Examples XIV to XIX, supra., were reconstituted with 5 ml of sterile water for injection. Their irritability, that is the muscular damage caused by their intramuscular administration, at the injection site was evaluated, using two animal species:

A—RABBITS: Shintain, S. et. al. method (Toxicol. and Appl. Pharmacology, 11, 293-301, 1967) was applied. Male albino rabbits weighing 2.5-3.5 kg were used. Reconstituted preparations were administered by intramuscular route. The procedure was repeated daily for 4 days using the same injection site. After the 4 days, the rabbit was sacrificed, the muscle was dissected and local tissue irritation was grossly scored from 0 to 5 according to the following criteria: score 0+no discernible gross reaction; score 1+slight hyperemia and discoloration; score 2=moderate hyperemia and discoloration; score 3=distinct discoloration in comparison with the color of the surrounding area; score 4=brown degeneration with small necrosis; score 5=widespread necrosis with an occasionally abscess of the muscle. The irritation was graded using the following categories: "none" for 0.4 or less; "slight" for 0.5-1.4; "mild" for 1.5-2.4; "moderate" for 2.5-3.4; "marked" for 3.5-4.4 and "severe" for 4.5 or more. Results of the evaluation were the following:

| PHARMACEUTIC COMPOSITION *ACTIVE INGREDIENTS | PROPORTION | EVALUATION SCORE | CATEGORY |
|---|---|---|---|
| Sulfamethoxazol-Trimethoprim | 5:1 | 2.33 | mild |
| Sulfisoxazol-Ormethoprim | 7:2 | 2.94 | moderate |
| Sulfadimethoxine-Trimethoprim | 5:1 | 1.66 | mild |
| Sulfamoxol-Trimethoprim | 5:1 | 1.38 | mild |
| Sulfaquinoxaline-Diaveridine | 4:1 | 1.67 | mild |
| Sulfadoxine-Ormethoprim | 7:1 | 2.34 | mild |
| Control (5 ml of pyrogen-free saline solution) | — | 0.0 | none |

*Sodium sulfonamides.

B—RATS: Kienel method (Arzneim. Forsch., 23, 263 (2), 1973) was used. Reconstituted preparations were administered once by intramuscular route. After 24 hours, and during 10 days, animals were then sacrificed observing local tissue injury and giving a score proportional to their diameter (Maximum injury degree has a score of 64). Results are shown in the following table:

| PHARMACEUTICAL COMPOSITION *ACTIVE INGREDIENTS | PROPORTION | EVALUATION SCORE | OBSERVATIONS |
|---|---|---|---|
| Sulfadimethoxine-Trimethoprim | 5:1 | 35 | Good muscular regeneration |
| Sulfadoxine-Ormethoprim | 7:1 | 42 | Good muscular regeneration |
| Sulfisoxazol-Ormethoprim | 7:2 | 41 | Good muscular regeneration |
| Sulfamethoxazol-Trimethoprim | 5:1 | 33 | Very good muscular reg. |
| Sulfaquinoxaline-Diaveridine | 4:1 | 42 | Moderate muscular reg. |
| Sulfamoxol-Trimethoprim | 5:1 | 38 | Good muscular regeneration |
| Control (5 ml of pyrogen-free | — | 12 | Without muscular injury |

| PHARMACEUTICAL COMPOSITION | | EVALUATION | |
|---|---|---|---|
| *ACTIVE INGREDIENTS | PROPORTION | SCORE | OBSERVATIONS |
| saline solution) | | | |

What is claimed:

1. A pharmaceutical composition, which comprises; in admixture, (a) from 1 to 20 parts by weight of an alkali metal sulfonamide, said sulfonamide having the structural formula:

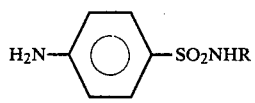

wherein R is selected from the group consisting of 6-methoxy-3-pyridazinyl, 6-ethoxy-3-pyridazinyl, 5,6-dimethoxy-4-pyrimidinyl, 2,6-dimethoxy-4-pyrimidinyl, 2,6-dimethyl-4-pyrimidinyl, 2-pyrimidinyl, 4,6-dimethyl-2-pyrimidinyl, 5-methoxy-2-pyrimidinyl, 3,4-dimethyl-5-isoxazolyl, 5-methyl-3-isoxazolyl, 4,5-dimethyl-2-oxazolyl and 2-quinoxalinyl; and (b) one part by weight of microcrystals of a potentiator for said sulfonamide, said potentiator being a 5-substituted 2,4-diaminopyrimidine of the formula:

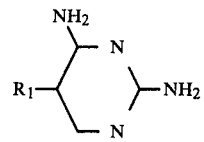

wherein $R_1$ is selected from the group consisting of 3,4,5-trimethoxybenzyl, 3,4-dimethoxy-6-methylbenzyl and 3,4-dimethoxybenzyl groups, said microcrystals being coated with a mixture of a phospholipid selected from the group consisting of phosphatidylcholine, both naturally occurring and synthetically prepared, phosphatidic acid, lysophosphatidylcholine, phosphatidylserine, phosphatidylethanolamine, sphingolipid, phosphatidylglycerol, spingomyelin, cardiolipin, glycolipid, ganglioside, cerebrosides and lecithin; and a non-ionic surface-active agent;

the proportion ratio between potentiator:phospholipid:surfactant being between 100:1:30 and 300:1:70.

2. The composition of claim 1 wherein said alkali metal is sodium.

3. The composition of claim 1 wherein the phospholipid is a lecithin.

4. The composition of claim 1 wherein the non-ionic surface-active agent is selected from the class consisting of monostearates and monopalmitates of polyoxyethylene sorbitan.

5. The composition of claim 1 which further comprises water for injection, said composition having a pH within the range of 8.5 to 9.5.

6. The composition of claim 1 wherein the sulfonamide is sulfadimethoxine and the potentiator is trimethoprim.

* * * * *